US00PP28421P3

(12) United States Plant Patent
Verwer

(10) Patent No.: US PP28,421 P3
(45) Date of Patent: Sep. 19, 2017

(54) ***DAHLIA* PLANT NAMED 'DAHLGR95'**

(50) Latin Name: *Dahlia hybrida*
Varietal Denomination: Dahlgr95

(71) Applicant: Aad W. M. Verwer, Lisse (NL)

(72) Inventor: Aad W. M. Verwer, Lisse (NL)

(73) Assignee: Verwer Dahlias B.V., Lisse (NL)

( * ) Notice: Subject to any disclaimer, the term of this patent is extended or adjusted under 35 U.S.C. 154(b) by 28 days.

(21) Appl. No.: 14/998,436

(22) Filed: Dec. 31, 2015

(65) Prior Publication Data

US 2017/0196155 P1 Jul. 6, 2017

(51) Int. Cl.
*A01H 5/02* (2006.01)

(52) U.S. Cl.
USPC ..... Plt./321

(58) Field of Classification Search
USPC ..... Plt./321
See application file for complete search history.

*Primary Examiner* — Susan McCormick Ewoldt
(74) *Attorney, Agent, or Firm* — C. A. Whealy

(57) ABSTRACT

A new and distinct cultivar of *Dahlia* plant named 'Dahlgr95', characterized by its relatively compact, mounding and dense plant habit; freely basal branching habit; dark green-colored leaves; early and freely flowering habit; single-type inflorescence form; large inflorescences with white-colored ray florets; and good postproduction longevity and garden performance.

2 Drawing Sheets

Botanical designation: *Dahlia hybrida.*
Cultivar denomination: 'DAHLGR95'.

BACKGROUND OF THE INVENTION

The present invention relates to a new and distinct cultivar of *Dahlia* plant, botanically known as *Dahlia hybrida*, and hereinafter referred to by the name 'Dahlgr95'.

The new *Dahlia* plant is a product of a planned breeding program conducted by the Inventor in Lisse, The Netherlands. The objective of the breeding program is to create new compact container and garden *Dahlia* plants with dark-colored leaves, large inflorescences and good postproduction longevity.

The new *Dahlia* plant originated from a cross-pollination conducted by the Inventor during the summer of 2010 of a proprietary seedling selection of *Dahlia hybrida* identified as code number VD5-241, not patented, as the female, or seed, parent with a proprietary seedling selection of *Dahlia hybrida* identified as code number VD5-272, not patented, as the male, or pollen, parent. The new *Dahlia* plant was discovered and selected by the Inventor as a single flowering plant from within the progeny of the stated cross-pollination in a controlled greenhouse environment in Lisse, The Netherlands during the summer of 2011.

Asexual reproduction of the new *Dahlia* plant by cuttings since February, 2012 in a controlled greenhouse environment in Lisse, The Netherlands, has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Dahlgr95'. These characteristics in combination distinguish 'Dahlgr95' as a new and distinct *Dahlia* plant:

1. Relatively compact, mounding and dense plant habit.
2. Freely basal branching habit.
3. Dark green-colored leaves.
4. Early and freely flowering habit.
5. Single-type inflorescence form.
6. Large inflorescences with white-colored ray florets.
7. Good postproduction longevity and garden performance.

Plants of the new *Dahlia* differ primarily from plants of the female parent selection in the following characteristics:

1. Plants of the new *Dahlia* are more compact than plants of the female parent selection.
2. Plants of the new *Dahlia* are denser and bushier than and not as open as plants of the female parent selection.
3. Plants of the new *Dahlia* and the female parent selection differ in ray floret color as the lower surface of ray florets of plants of the female parent selection are lilac in color.

Plants of the new *Dahlia* differ primarily from plants of the male parent selection in the following characteristics:

1. Plants of the new *Dahlia* are taller than plants of the male parent selection.
2. Plants of the new *Dahlia* and the male parent selection differ in leaf color as plants of the male parent selection have bronze-colored leaves.
3. Plants of the new *Dahlia* and the male parent selection differ in ray floret color as plants of the male parent selection have brownish red and golden yellow bicolored ray florets.

Plants of the new *Dahlia* can be compared to plants of the *Dahlia hybrida* 'HS Princess', disclosed in U.S. Plant Pat.

No. 20,567. In side-by-side comparisons conducted in Lisse, The Netherlands, plants of the new *Dahlia* differed from plants of 'HS Princess' in the following characteristics:

1. Plants of the new *Dahlia* were more compact than plants of 'HS Princess'.
2. Plants of the new *Dahlia* had thicker lateral branches than plants of 'HS Princess'.
3. Leaves and leaflets of plants of the new *Dahlia* were larger and darker in color than leaves and leaflets of plants of 'HS Princess'.
4. Plants of the new *Dahlia* flowered about five days later than plants of 'HS Princess'.
5. Plants of the new *Dahlia* had slightly larger inflorescences than plants of 'HS Princess'.
6. Plants of the new *Dahlia* and 'HS Princess' differed in ray floret color as plants of 'HS Princess' had blush pink to white-colored ray florets.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet comprises a side perspective view of a typical flowering plant of 'Dahlgr95' grown in an outdoor nursery.

The photograph on the second sheet is a close-up view of a typical flowering plant of 'Dahlgr95'.

DETAILED BOTANICAL DESCRIPTION

The photographs and following observations and measurements describe plants grown during the late summer and early autumn in ground beds in an outdoor nursery in Lisse, The Netherlands and under cultural practices typical of commercial *Dahlia* production. During the production of the plants, day temperatures ranged from 15° C. to 30° C. and night temperatures ranged from 7° C. to 20° C. Plants were pinched one time about three weeks after planting. Plants were three months old when the photographs were taken and four months old when the description was taken. In the following description, color references are made to The Royal Horticultural Society Colour Chart, 1995 Edition, except where general terms of ordinary dictionary significance are used.

Botanical classification: *Dahlia hybrida* 'Dahlgr95'.

Parentage:

*Female, or seed, parent*.—Proprietary seedling selection of *Dahlia hybrida* identified as code number VD5-241, not patented.

*Male, or pollen, parent*.—Proprietary seedling selection of *Dahlia hybrida* identified as code number VD5-272, not patented.

Propagation:

*Type*.—By vegetative cuttings.

*Time to initiate roots, summer*.—About twelve days at soil temperatures about 15° C. and air temperatures ranging from about 15° C. to 25° C.

*Time to initiate roots, winter*.—About 13 to 14 days at soil temperatures about 15° C. and air temperatures ranging from about 15° C. to 25° C.

*Time to produce a rooted young plant, summer*.—About 20 days at soil temperatures about 15° C. and air temperatures ranging from about 15° C. to 25° C.

*Time to produce a rooted young plant, winter*.—About 21 days at soil temperatures about 15° C. and air temperatures ranging from about 15° C. to 25° C.

*Root description*.—Fine, fleshy.

*Rooting habit*.—Moderately freely branching; dense.

*Tubers*.—Length: About 15 cm. Diameter: About 16 cm. Texture: Corky. Color: Close to 159B.

Plant description:

*Plant and growth habit*.—Relatively compact and mounding plant habit; appropriate for 20-cm containers; inverted triangular plant form; freely basal branching with about six primary lateral branches developing per plant; dense and bushy appearance; inflorescences held above the foliar plane on strong peduncles; vigorous growth habit.

*Plant height*.—About 60 cm.

*Plant diameter or spread*.—About 30 cm.

*Lateral branches*.—Length: About 40 cm. Diameter: About 1.8 cm. Internode length: About 6 cm to 12 cm. Texture: Smooth, glabrous. Luster: Semi-glossy. Strength: Strong. Aspect: Erect to about 20° from vertical. Color: Close to 148A; towards the apex, heavily tinged with close to 187A.

Leaf description:

*Arrangement*.—Opposite, simple or compound with three or five leaflets per leaf.

*Leaf length, simple leaves*.—About 10 cm.

*Leaf width, simple leaves*.—About 23 cm.

*Leaf length, compound leaves with three leaflets*.—About 13 cm.

*Leaf width, compound leaves with three leaflets*.—About 4.5 cm.

*Leaf length, compound leaves with five leaflets*.—About 23 cm.

*Leaf width, compound leaves with five leaflets*.—About 4.5 cm.

*Shape, simple leaves or leaflets*.—Ovate.

*Apex, simple leaves or leaflets*.—Acuminate.

*Base, simple leaves or leaflets*.—Attenuate.

*Margin, simple leaves or leaflets*.—Serrate; sinuses divergent.

*Venation pattern, simple leaves or leaflets*.—Pinnate, reticulate.

*Texture, upper and lower surfaces, simple leaves or leaflets*.—Smooth, glabrous.

*Color*.—Developing leaves or leaflets, upper surface: Darker than 147A. Developing leaves or leaflets, lower surface: Close to 148A. Fully expanded leaves or leaflets, upper surface: Close to 147A tinged with close to 187B; venation, close to 147B. Fully expanded leaves or leaflets, lower surface: Close to 187B; venation, close to 187C.

*Petioles*.—Length, simple leaves or leaflets: About 6 cm. Diameter, simple leaves or leaflets: About 5 mm. Texture, upper and lower surfaces, simple leaves or leaflets: Smooth, glabrous. Color, simple leaves or leaflets, upper and lower surfaces: Close to 187A.

Inflorescence description:

*Appearance and flowering habit*.—Single-type inflorescences with ray and disc florets developing acropetally on a receptacle; inflorescences positioned above and beyond the foliar plane on strong peduncles; inflorescences face upright to outwardly; freely flowering habit with typically about 28 inflorescences developing per plant during the flowering season.

*Fragrance*.—None detected.

*Time to flower*.—Early flowering habit; plants begin flowering about 70 days after planting; flowering continuous during the summer and autumn in The Netherlands.

*Post-production longevity*.—Good postproduction longevity; inflorescences maintain good substance for about twelve days on the plant and for about four days as a cut flower; inflorescences persistent.

*Inflorescence buds*.—Height: About 1.1 cm. Diameter: About 1.9 cm. Shape: Oblate. Texture: Smooth, glabrous. Color: Towards the base, close to 200B; mid-section, close to 164B; and towards the apex, close to 158B.

*Inflorescence diameter*.—Large, about 9.4 cm.

*Inflorescence depth* (*height*).—About 2.1 cm.

*Disc diameter*.—About 2.1 cm.

*Receptacle height*.—About 6 mm.

*Receptacle diameter*.—About 1.8 cm.

*Ray florets*.—Number of ray florets per inflorescence: About eight arranged in a single whorl. Length: About 4.3 cm. Width: About 2.6 cm. Shape: Ovate. Apex: Obtuse or mucronulate. Base: Attenuate. Margin: Entire. Aspect: Initially upright to roughly perpendicular to the peduncle. Texture and luster, upper and lower surfaces: Smooth, glabrous; velvety to shiny. Color: When opening, upper surface: Close to 158B; occasional spots at the margins, close to 73A. When opening, lower surface: Close to 158C; venation, close to 73A. Fully opened, upper surface: Close to 155B; at the base, close to 3A; venation, close to 3A; color does not change with development. Fully opened, lower surface: Close to 155A; venation, close to 73B.

*Disc florets*.—Number of disc florets per inflorescence: About 95. Length: About 1.4 cm. Diameter: About 2 mm. Shape: Tubular; apex dentate, pentafid. Aspect: Mostly upright. Texture: Smooth, glabrous. Color, immature: Close to 17B. Color, mature: Close to 21A; venation, close to 1B.

*Phyllaries*.—Quantity per inflorescence: About five arranged in a single whorl. Length: About 1.7 cm. Width: About 7 mm. Shape: Ovate. Apex: Acuminate. Base: Attenuate. Margin: Entire. Texture, upper and lower surfaces: Smooth, glabrous. Color, upper and lower surfaces: Close to 200A.

*Peduncles*.—Length, terminal peduncle: About 30 cm. Diameter, terminal peduncle: About 1.6 cm. Length, third peduncle: About 20 cm. Diameter, third peduncle: About 1.2 mm. Strength: Strong. Aspect: Mostly erect to 20° from vertical. Texture: Smooth, glabrous. Color: Close to 187A.

*Reproductive organs*.—Androecium, present on disc florets only: Quantity per disc floret: Five. Filament length: About 7 mm. Filament color: Close to 3D. Anther length: About 4 mm. Anther shape: Lanceolate. Anther color: Close to 2C. Pollen amount: Moderate. Pollen color: Close to 17A. Gynoecium, present on ray and disc florets: Quantity per floret: One. Pistil length: About 1.6 cm. Stigma shape: Lanceolate. Stigma color: Close to 4C. Style length: About 9 mm. Style color: Close to 1D. Ovary color: Close to 4D.

*Seeds*.—Seed development has not been observed on plants of the new *Dahlia*.

Disease & pest resistance: Plants of the new *Dahlia* have not been shown to be resistant to pathogens and pests common to *Dahlia* plants.

Garden performance: Plants of the new *Dahlia* have exhibited good tolerance to rain and wind and have been observed to tolerate temperatures from about 0° C. to about 35° C.

It is claimed:

1. A new and distinct *Dahlia* plant named 'Dahlgr95' as illustrated and described.

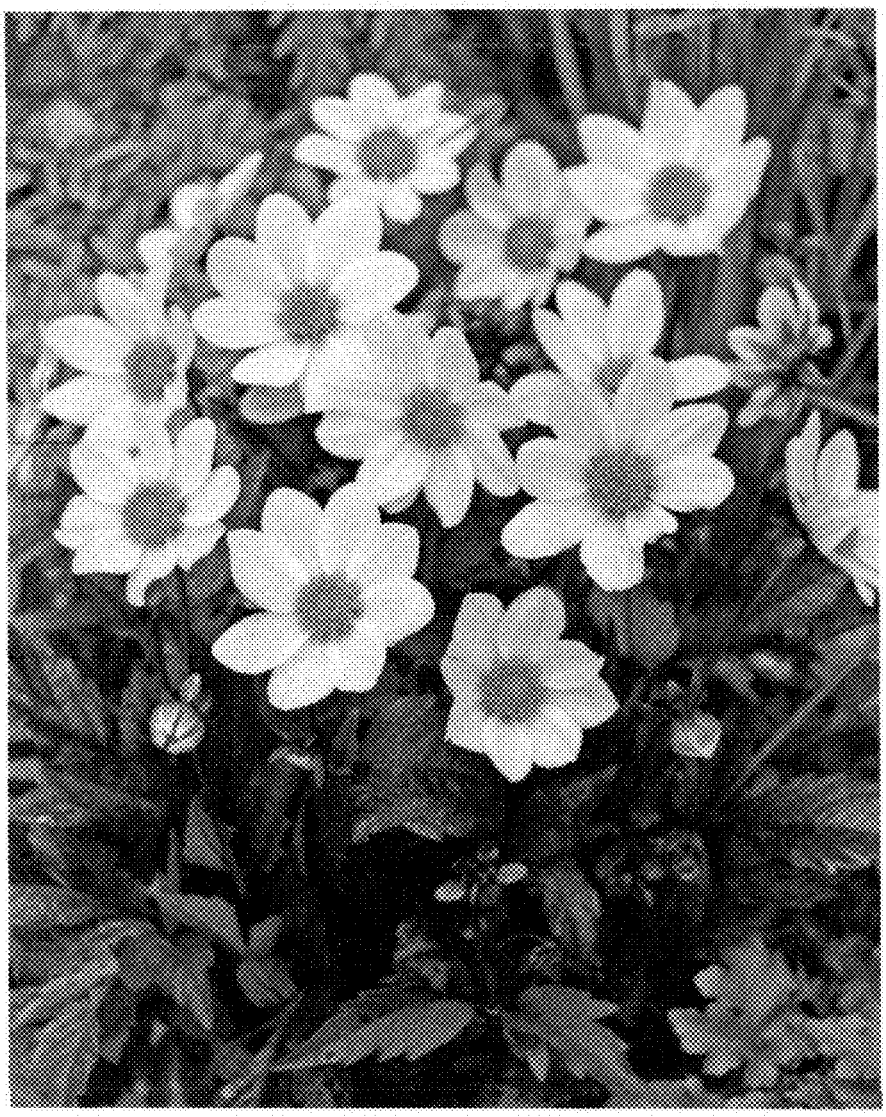

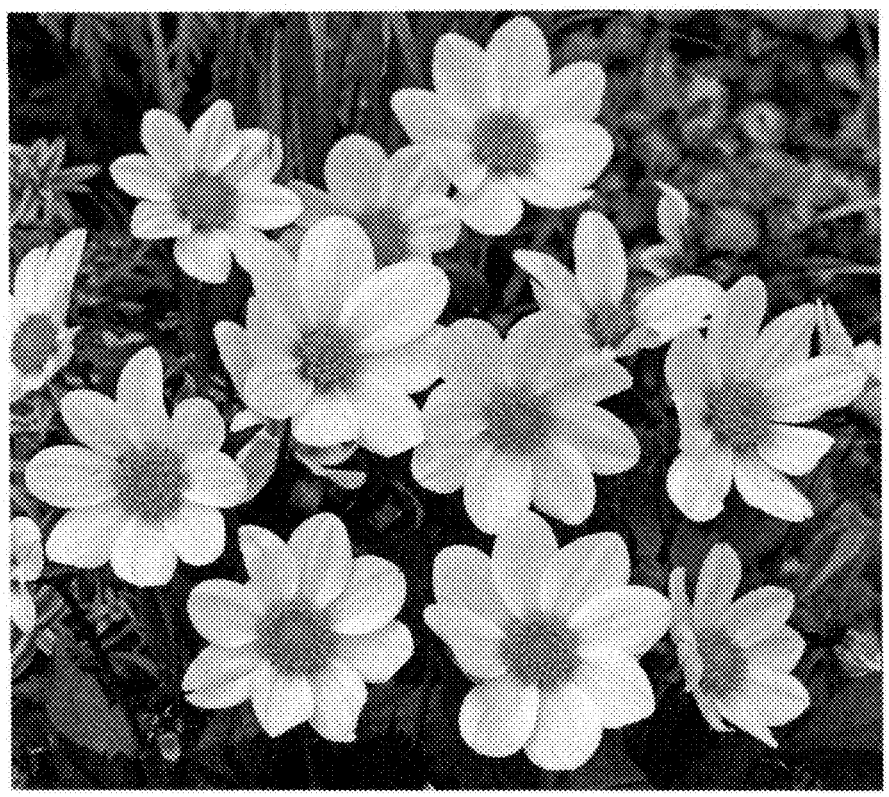

* * * * *